US006986841B2

(12) United States Patent
Zare et al.

(10) Patent No.: US 6,986,841 B2
(45) Date of Patent: Jan. 17, 2006

(54) FUSED-SILICA CAPILLARIES WITH PHOTOPOLYMER COMPONENTS

(76) Inventors: Richard N. Zare, 724 Santa Ynez, Stanford, CA (US) 94305; Maria T. Dulay, 955-E La Mesa Ter., Sunnyvale, CA (US) 94086; Jing-Ran Chen, 1247 Cranbrook Dr., Shaumburg, IL (US) 60193

( * ) Notice: Subject to any disclaimer, the term of this patent is extended or adjusted under 35 U.S.C. 154(b) by 174 days.

(21) Appl. No.: 10/674,652

(22) Filed: Sep. 29, 2003

(65) Prior Publication Data

US 2004/0055940 A1 Mar. 25, 2004

Related U.S. Application Data

(63) Continuation of application No. 10/008,482, filed on Nov. 13, 2001, now abandoned, which is a continuation of application No. 09/507,707, filed on Feb. 18, 2000, now abandoned.

(51) Int. Cl.
  *B01D 15/08* (2006.01)

(52) U.S. Cl. .................... 210/198.2; 210/635; 210/656; 96/101

(58) Field of Classification Search ................ 210/635, 210/656, 198.2; 95/82, 88; 96/101; 204/601, 204/605, 451, 455
  See application file for complete search history.

(56) References Cited

U.S. PATENT DOCUMENTS

| 3,503,712 A | 3/1970 | Sussman ...................... 23/252 |
| 3,568,840 A | 3/1971 | Hashimoto et al. ...... 210/198.2 |
| 3,757,490 A | 9/1973 | Ma .............................. 55/67 |
| 3,808,125 A | 4/1974 | Good ...................... 210/198.2 |
| 3,878,092 A | 4/1975 | Fuller ....................... 210/31 C |
| 4,293,415 A | * 10/1981 | Bente et al. ............. 210/198.2 |
| 4,323,439 A | 4/1982 | O'Farrell ................. 204/180 G |
| 4,617,102 A | 10/1986 | Tomblin et al. ........ 204/299 R |
| 4,675,300 A | 6/1987 | Zare et al. .................. 436/172 |
| 4,790,919 A | 12/1988 | Baylor, Jr. ............... 204/182.8 |
| 4,793,920 A | 12/1988 | Cortes |
| 5,085,756 A | 2/1992 | Swedberg ............... 204/299 R |
| 5,116,471 A | 5/1992 | Chien et al. ............. 204/180.1 |
| 5,116,495 A | 5/1992 | Prohaska ................. 210/198.2 |

(Continued)

FOREIGN PATENT DOCUMENTS

| EP | 0 439 318 | 7/1991 |
| EP | 0 779 512 | 6/1997 |
| WO | WO 98/29350 | 7/1998 |
| WO | WO 99/30147 | 6/1999 |
| WO | WO 00/49396 | 8/2000 |

OTHER PUBLICATIONS

C. Yu et al., "Towards Stationary Phases for Chromatography on a Microchip: Molded Porous Polymer Monoliths Prepared in Capillaries by Photoinitiated In Situ Polymerization as Separation Media for Electrochromatography," *Electrophoresis*, vol. 21, 2000, pp. 120–127.

J. Quirino et al., "Sweeping of Analyte Zones in Electrokinetic Chromatography," *Analytical Chemistry*, vol. 71, No. 8, Apr. 15, 1999, pp. 1638–1644.

M. Taylor et al., "Analysis of Corticosteroids in Biofluids by Capillary Electrochromatography with Gradient Elution," *Analytical Chemistry*, vol. 69, No. 13, Jul. 1, 1997, pp. 2554–2558.

(Continued)

*Primary Examiner*—Ernest G. Therkorn

(57) ABSTRACT

A separation column is provided with a photopolymer component which, when irradiated, causes controlled porosity polymerization. A particularly preferred embodiment is wherein the separation medium is retained by a photopolymer frit, which can be reliably and reproducibly generated with controlled porosity.

10 Claims, 4 Drawing Sheets

U.S. PATENT DOCUMENTS

| | | | |
|---|---|---|---|
| 5,135,627 A | 8/1992 | Soane | 204/182.8 |
| 5,200,150 A | 4/1993 | Rose, Jr. | 422/62 |
| 5,202,010 A | 4/1993 | Guzman | 204/299 R |
| 5,308,495 A | 5/1994 | Avnir et al. | 210/656 |
| 5,316,680 A | 5/1994 | Frechet et al. | 210/635 |
| 5,334,310 A | 8/1994 | Frechet et al. | 210/198.2 |
| 5,340,452 A | 8/1994 | Brenner et al. | 204/180.1 |
| 5,423,966 A | 6/1995 | Wiktorowicz | 204/182.8 |
| 5,453,185 A | 9/1995 | Frechet et al. | 210/198.2 |
| 5,453,382 A | 9/1995 | Novotny et al. | 436/178 |
| 5,552,994 A | 9/1996 | Cannon et al. | 210/635 |
| 5,599,445 A | 2/1997 | Betz et al. | 210/198.2 |
| 5,605,649 A | 2/1997 | Stohrer et al. | |
| 5,624,875 A | 4/1997 | Nakanishi et al. | |
| 5,637,135 A | 6/1997 | Ottenstein et al. | 96/101 |
| 5,647,979 A | 7/1997 | Liao et al. | 210/198.2 |
| 5,667,674 A | 9/1997 | Hanggi et al. | 210/198.2 |
| 5,719,322 A | 2/1998 | Lansbarkis et al. | 73/23.39 |
| 5,728,296 A | 3/1998 | Hjerten et al. | 210/198.2 |
| 5,728,457 A | 3/1998 | Frechet et al. | 428/310.5 |
| 5,759,405 A | 6/1998 | Anderson, Jr. et al. | 210/656 |
| 5,766,435 A | 6/1998 | Liao et al. | 204/451 |
| 5,772,875 A | 6/1998 | Pettersson et al. | 210/198.2 |
| 5,800,692 A | 9/1998 | Naylor et al. | 204/601 |
| 5,858,241 A | 1/1999 | Dittmann et al. | 210/656 |
| 5,916,427 A | 6/1999 | Kirkpatrick | 204/469 |
| 5,938,919 A * | 8/1999 | Najafabadi | 210/198.2 |
| 6,136,187 A | 10/2000 | Zare et al. | 210/198.2 |
| 6,210,570 B1 | 4/2001 | Holloway | |
| 6,398,962 B1 | 6/2002 | Cabrera et al. | |
| 6,402,918 B1 | 6/2002 | Schlenoff | |
| 6,531,060 B1 | 3/2003 | Nakanishi | |
| 6,562,744 B1 | 5/2003 | Nakanishi | |
| 2002/0079257 A1 | 6/2002 | Zare et al. | |

OTHER PUBLICATIONS d.A. Stead et al., "Capillary Electrochromatography of Steroids Increased Sensitivity by On–Line Concentration and Comparison with High–Performance Liquid Chromatography," *Journal of Chromatography A.* vol. 798. 1998, pp. 259–267.

Y. Zhang et al., "High–Efficienty On–Line Concentration Technique of Capillary Electrochromatography," *Analytical Chemistry,* vol. 72, No. 22, Nov. 15, 2000, pp. 5744–5747.

T. Tegeler et al. "On–Column Trace Enrichment by Sequential Frontal and Elution Electrochromatography. 1. Application to Carbamate Insecticides," *Analytical Chemistry,* vol. 73, No. 14, Jul. 15, 2001, pp. 3365–3372.

F. E. P. Mikkers et al., "Concentration Distributions in Free Zone Electrophoresis," *Journal of Chromatography,* vol. 169, Feb. 1, 1979, pp. 1–10.

R.–L. Chien et al., "On–Column Sample Concentration Using Field Amplification In CZE," *Analytical Chemistry,* vol. 64, No. 8, Apr. 15, 1992, pp. 489–496A.

J. Quirino et al., "Exceeding 5000–Fold Concentration of Dilute Analytes in Micellar Electrokinetic Chromatography," *Science,* vol. 282, Oct. 16, 1998, pp. 465–468.

C. Yang et al., "Electrically Driven Microseparation Methods for Pesticides and Metabolites. II: On–line and Off–line Preconcentration of Urea Herbicides in Capillary Electrochromatography," *Electrophoresis,* vol. 20, 1999, pp. 2337–2342.

M. Dulay et al., "Preparation and Characterization of Monolithic Porous Capillary Columns Loaded with Chromatographic Particles," *Analytical Chemistry,* vol. 70, No. 23, Dec. 1, 1998, pp. 5103–5107.

M. Dulay et al., "Photopolymerzed Sol–Gel Monoliths for Capillary Electrochromatography," *Analytical Chemistry,* vol. 73, No. 16, Aug. 15, 2001, pp. 3921–3926.

J. Quirino et al., "New Strategy for On–Line Preconcentration in Chromatographic Separations," manuscript undated.

J. Quirino et al., "On–Line Preconcentration in Capillary Electrochromatography Using a Porous Monolith, Solvent Gradient and Sample Stacking," manuscript undated.

M. Kato et al, "Photopolymerized Sol–Gel Frits for Packed Columns in Capillary Electrochromatography," *Journal of Chromatography A,* vol. 924, 2001, pp. 187–195.

J.–R. Chen et al., "Macroporous Photopolymer Frits for Capillary Electrochromatography," *Analytical Chemistry,* vol. 72, No. 6, Mar. 15, 2000, pp. 1224–1227.

C. Viklund et al., "Molded Macroporous Poly(Glycidyl Methacrylate–Co–Trimethylolpropane Trimethacrylate) Materials with Fine Controlled Porous Properties: Preparation of Monoliths Using Photoinitiated Polymerization," *Chem. Mater.,* vol. 9, No. 2, 1997, pp. 463–471.

M. Dulay et a.l, "Bonded–Phase Photopolymerized Sol–Gel Monoliths for Reversed Phase Capillary Electrochromatography," *J. Sep. Sci.,* vol. 25, 2002, pp. 3–9.

M. Kato et al., "Effect of Preparatory Conditions on the Performance of Photopolymerized Sol–Gel Monoliths for Capillary Electrochromatography," *Journal of Chromatography A,* vol. 961, 2002, pp. 45–51.

M. Kato et al., "Enantiomeric Separation of Amino Acids and Nonprotein Amino Acids Using a Particle–Loaded Monolithic Column," *Electrophoresis,* vol. 21, 2000, pp. 3145–3151.

J. Quirino et al., "On–Line Preconcentration in Capillary Electrochromatography Using a Porous Monolith Together with Solvent Gradient and Sample Stacking," *Anal. Chem.,* vol. 73, 2001, pp. 5557–5563.

J. Quirino et al., "Strategy for On–Line Preconcentration in Chromatographic Separations," *Anal. Chem.,* vol. 73, 2001, pp. 5539–5543.

K. Morishima et al., "Toward Sol–Gel Electrochromatographic Separations on a Chip," *J. Sep. Sci.,* vol. 25, 2002, pp. 1226–1230.

M.J. Hilhorst, et al., "Sensitivity Enhancement in Capillary Electrochromatography by On–Column Preconcentration," *Chromatographia 2001, 53,* Feb. (No. ¾), pp. 190–196.

Woo, et al., "Photpolymerization of Methyl Methacrylate with Primary Aryl– and Alklylsilanes," *Bulletin of the Korean Chemical Society,* vol. 16, No. 11, ISSN 0253–2964, Nov. 20, 1995, pp. 1057 & 1059.

Cikalo, et al., "Capillary Electrochromatography," *Analyst, Jul. 1998,* vol. 123 pp. 87R–102R.

Quirino, et al., "Sample Stacking of Cationic and Anionic Analytes in Capillary Electrophoresis," *Journal of Chromatography,* A, 902 2000, pp. 119–135.

Quirino, et al. "Sweeping of Neutral Analytes in Electrokinetic Chromatography with High–Salt–Containing Matrixes," *Analytical Chemistry,* vol. 72, No. 8, Apr. 15, 2000.

Chen, et al., "Semipreparative Capillary Electrochromatography." *Analytical Chemistry,* vol. 73, No. 9, May 1, 2001 1987–1992.

Colon, et al., "Packing Columns for Capillary Electrochromatography," *Journal of Chromatography,* A. 887 (2000) pp. 43–53.

Svec, et al., "Design of the Monolithic Polymers used in Capillary Electrochromatography Columns," *Journal of Chromatography,* A, 887 (2000) pp. 3–29.

Constantin, et al., "Preparation of Stationary Phasese for Open–Tubular Capillary Electrochromatography Using the Sol–Gel Method," *Journal of Chromatography,* A, 887 (2000) pp. 253–263.

Tan, et al., "Preparation and Evaluation of Bonded Linear Polymethacrylate Stationary Phases for Open Tubular Capillary Electrokinetic Chromatography," *Analytical Chemistry,* vol. 69, No. 4, Feb. 15, 1997. pp. 581–586.

Chirica, et al., "Fritless Capillary Columns for HPLC and CEC Prepared by Immobilizing the Stationary Phase in an Organic Polymer Matrix," *Analytical Chemistry,* vol. 72, No. 15, Aug. 1, 2000, pp. 3605–3610.

Palm, et al., Macroporous Polyacrylamide/Poly(ethylene glycol) Matrixes as Stationary Phases in Capillary Electrochromatography, *Analytical Chemistry,* vol. 69, No. 22, Nov. 15, 1997, pp. 4499–4507.

Hayes, et al., "Sol–Gel Monolithic Columns with Reversed Electroosmotic Flow for Capillary Electrochromatography," *Analytical Chemistry,* vol. 72, No. 17, Sep. 1, 2000, pp. 4090–4099.

Mol, et al., "Trace Level Analysis of Micropollutants in Aqueous Samples using Gas Chromatography with On–Line Sample Enrichment and Large Volume Injection," *Journal of Chromatography A,* 703 (1995) pp. 277–307.

Quirino, et al., "Approaching a Million–Fold Sensitivity Increase in Capillary Electrophoresis with Direct Ultraviolet Detection: Cation–Selective Exhaustive Injection and Sweeping," *Analytical Chemistry,* vol. 72, No. 5, Mar. 1, 2000, pp. 1023–1030.

Rudge, et al., "Solute Retention in Electrochromatography by Electrically Induced Sorption," *AIChE Journal,* May 1993, vol. 39, No. 5, pp. 797–808.

Kitagawa, et al., "Voltage–Induced Sample Release from Anion Exchange Supports in Capillary Electrochromatography," *Analytical Sciences,* Jun. 1998, vol. 14, pp. 571–575.

Josic, et al., "Monoliths as Stationary Phases for Separation of Proteins and Polynucleotides and Enzymatic Conversion," *Journal of Chromatography* B, 752 (2001) pp. 191–205.

Peters, et al., "Molded Rigid Polymer Monoliths as Separation Media for Capillary Electrochromatography," *Analytical Chemistry,* vol. 69, No. 17, Sep. 1, 1997 3646–3649.

Dulay, et al., "Automated Capillary Alectrochromatography: Reliability and Reproducibility Studies," *Journal of Chromatography A,* 725 (1996) pp. 361–366.

Brinker, et al., "Sol–Gel Science: The Physics and Chemistry of Sol–Gel Processing," *Academic Press,* San Diego, pp. 372–385, 408–411, 458–459 1990.

Badini, et al., "Impregnation of a pH–Sensitive Dye into Sol–Gels for Fibre Optic Chemical Sensors," *Analyst, 120,* pp. 1025–1028, Apr. 1995.

Snyder, Introduction to Modern Liquid Chromatography, *John Wiley & Sons, Inc.,* New York, 1979, pp. 145–147.

International Search Report mailed Oct. 25, 2002.

Boughtflower et al., "Capillary Electrochromatography—Some Important Considerations in the Preparation of Packed Capillaries and the Choice of Mobile Phase Buffers," *Chromatographia,* vol. 40, No. 5/6, Mar. 1995, pp. 329–335.

Notification of First Office Action (in English), The Patent Office of the People's Republic of China, mailed Sep. 30, 2005, Application No. 02818591.9 for the Board of Trustees of the Leland Stanford Junior University, 5 pages.

Listing of claims pending in Application No. 02818591.9, on the date of the Notification of First Office Action therein (see above), 8 pages.

Ngola et al., "Conduct–as–Cast Polymer Monoliths as Separation Media for Capillary Electrochromatography,"*Analytical Chemistry,* vol. 73, No. 5, Mar. 1, 2001, pp. 849–856.

Supplementary European Search Report, Application No. EP 02 76 1357 for The Board of Trustees of the Leland Stanford Junior University mailed Aug. 1, 2005.

Supplementary Search Report mailed Dec. 16, 2004 for European Application No. 02 76 8529 for the Board of Trustees of the Leland Stanford Junior College.

Notification of Transmittal of the International Search Report of the Declaration mailed Jan. 3, 2003 for International Application No. PCT/US02/25752 for The Board of Trustees of the Leland Stanford Junior College.

* cited by examiner

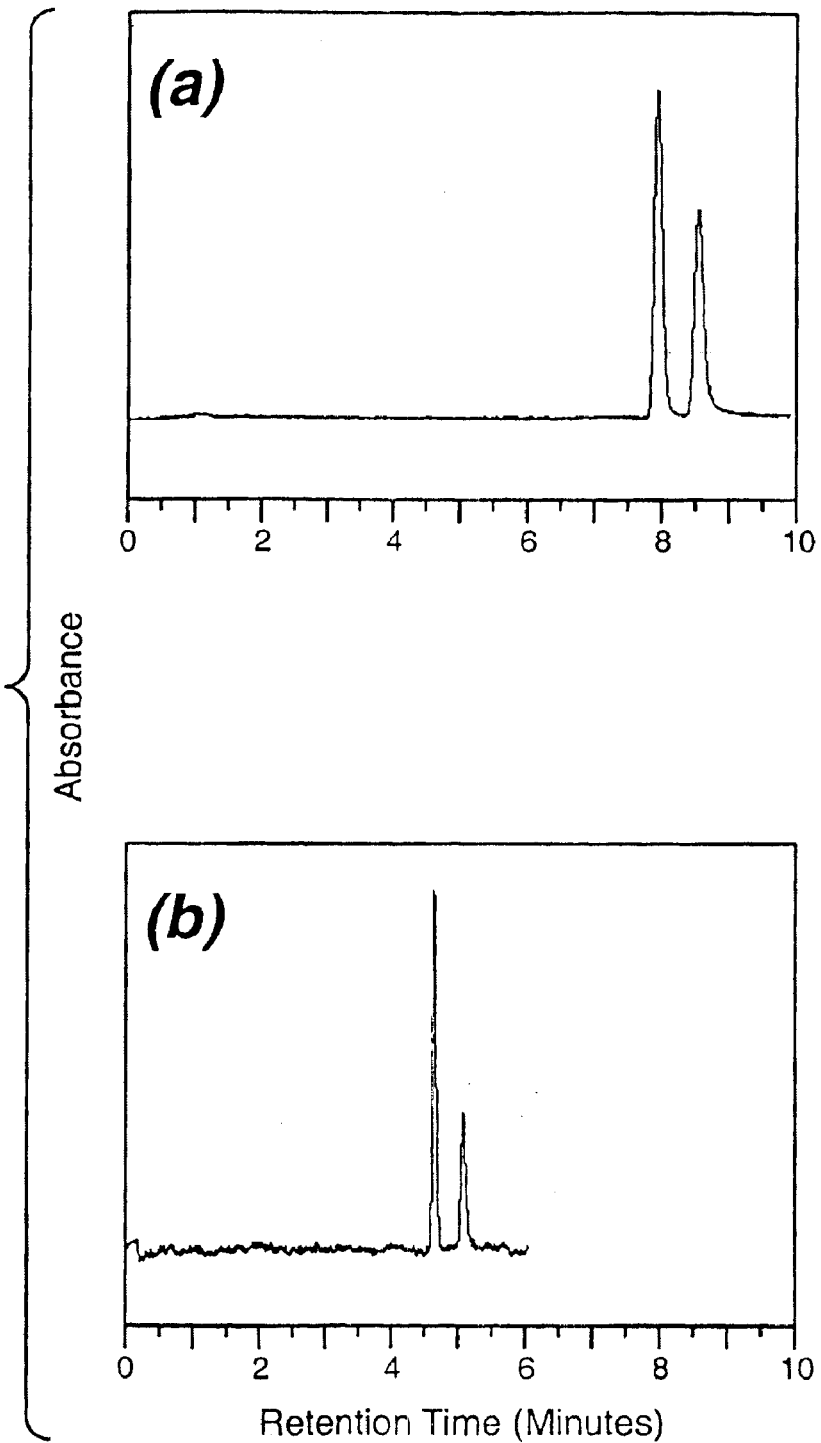
FIG._2

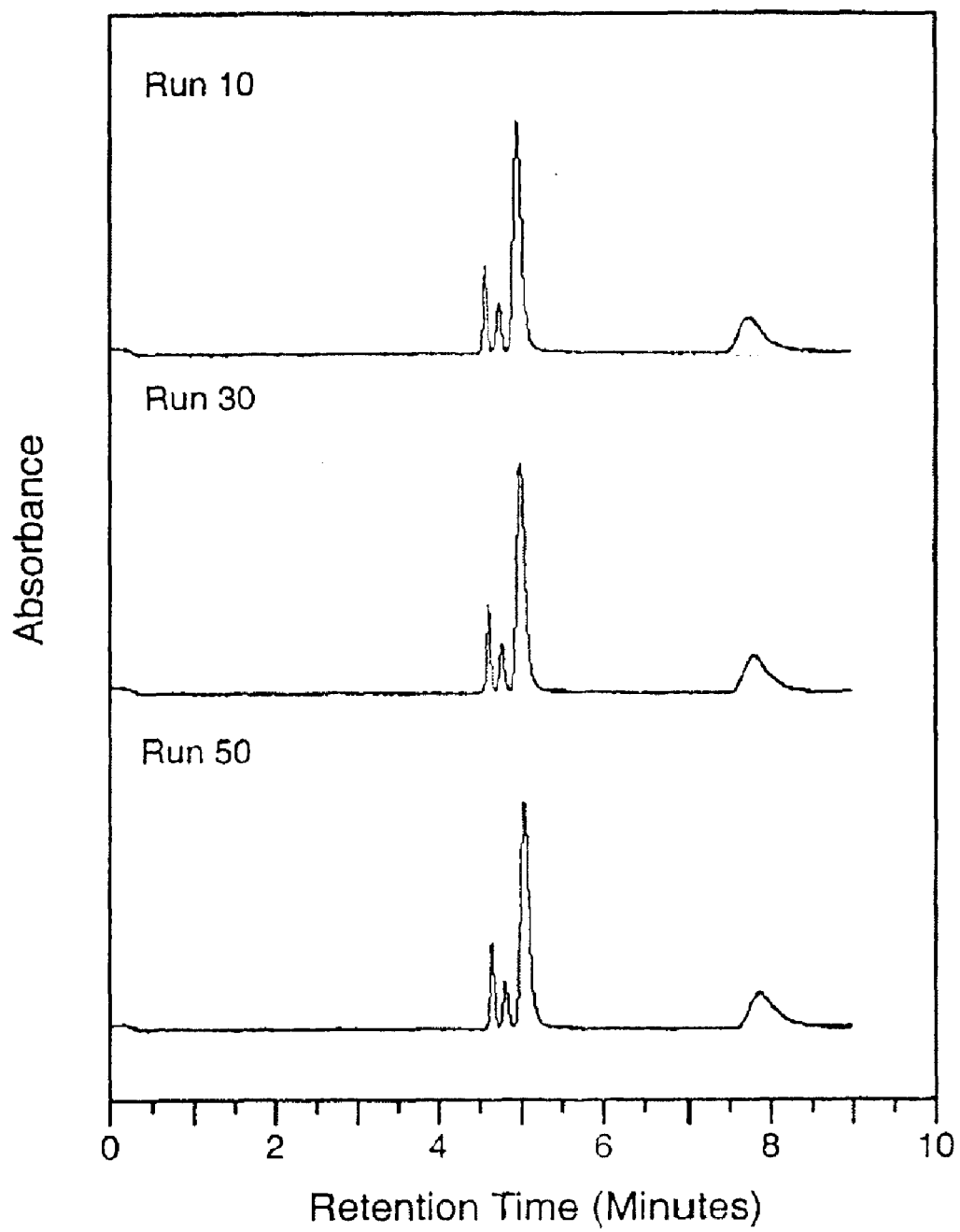
FIG._3

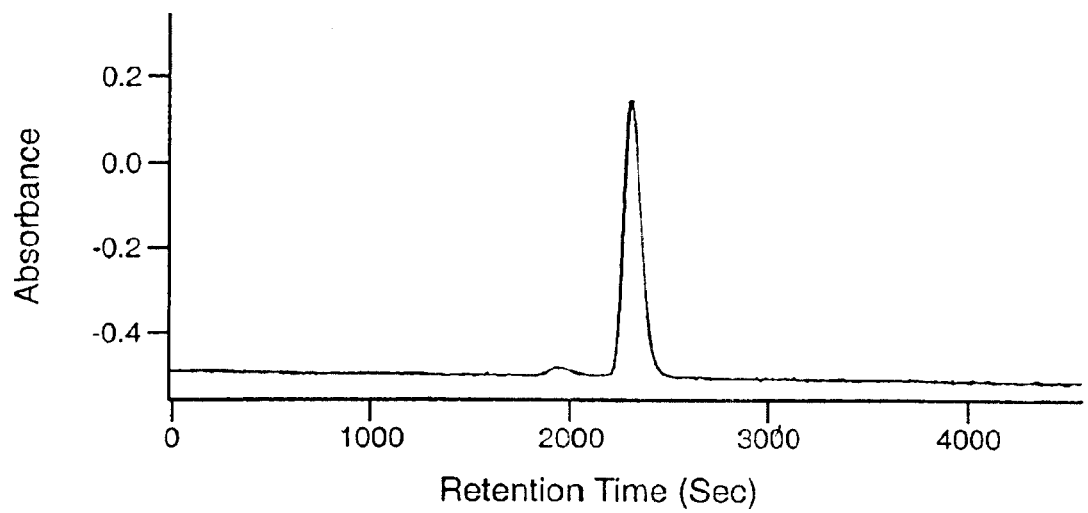
FIG._4A
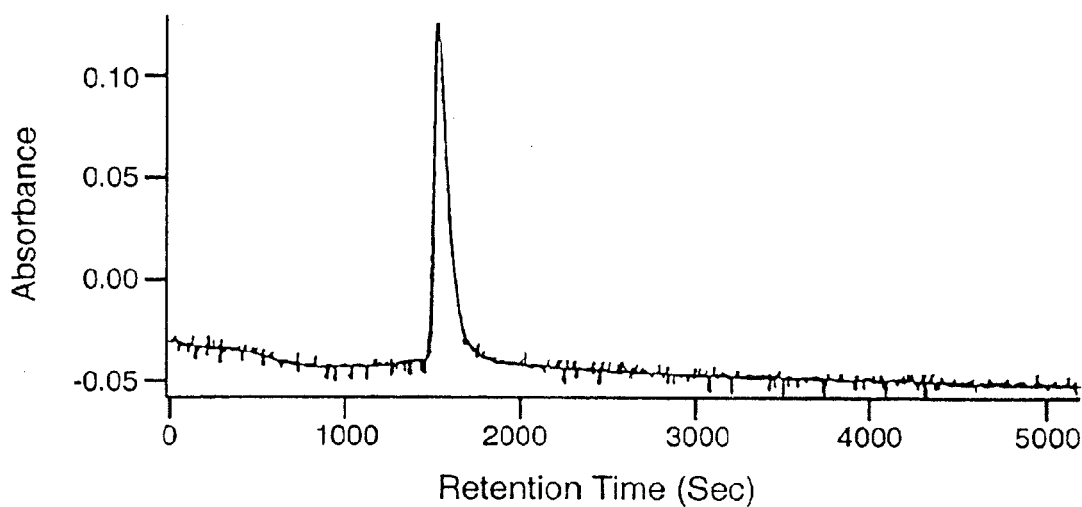
FIG._4B

FUSED-SILICA CAPILLARIES WITH PHOTOPOLYMER COMPONENTS

CROSS REFERENCE TO RELATED APPLICATIONS

This is a continuation of application Ser. No. 10/008,482, filed Nov. 13, 2001, now abandoned which is in turn a continuation of application Ser. No. 09/507,707, filed Feb. 18, 2000, both abandoned and both of which are incorporated herein in there entireties by this reference.

BACKGROUND OF THE INVENTION

1. Field of the Invention

This invention generally relates to separation columns, particularly capillaries useful in capillary zone electrophoresis, including capillary electrochromatography, and more particularly to separation columns that includes a photopolymer component. This photopolymer component may be in the form of a frit.

2. Description of Related Art

Over the past decade, capillary zone electrophoresis (CZE), with its high peak capacity (i.e., the number of peaks separated per unit time), has developed into a powerful and widely used technique for separating ionic species by their electrophoretic mobilities. The lack of selectivity for uncharged analytes in CZE, however, has remained more problematic. Several methods have been developed, such as micellar electrokinetic chromatography (MEKC), to help overcome this problem by providing a pseudostationary phase in which uncharged compounds can be separated. The application of methods such as MEKC is limited because of the restricted number of pseudostationary phases that can be employed in this technique.

With the advent of capillary electrochromatography (CEC), where both chromatographic and electrophoretic transport mechanisms are combined, separation and analysis of mixtures of uncharged analytes can be achieved using low sample volumes with high resolution and efficiency. The increased interest in CEC for analytical applications arises from the large plate numbers and relatively high separation speeds achieved and the wide range of stationary phases (those commonly used in high-performance liquid chromatography) that can be used.

Many groups have reported on the use of slurry or electrokinetic packing methods for the fabrication of electrochromatography capillary columns with typical inner diameters of 75 $\mu$m. Reversed-phase capillary columns have been prepared, typically with octadecyl silica (ODS) whose particle diameters are on the order of 1.5 to 5 $\mu$m. In both packing techniques, the use of retaining frits at both the inlet and the outlet of the capillary has been required to prevent the chromatographic packing material from exiting the capillary. Although systematic studies regarding the effects of the frits on the performance of such capillaries have not been reported, it is thought that these frits may degrade the efficiencies of these capillary columns.

Alternative approaches have been reported for the preparation of capillary columns that avoid the technical problems of frit fabrication and column preparation associated with slurry and electrokinetic packing. One approach uses bonded stationary phases. Capillary columns prepared in this manner, however, suffer from low retention and low sample capacities as well as long preparation times. An alternative method for the preparation of open tubular capillary columns uses monolithic packing technology. For example, Dulay et al. have described the preparation and characterization of monolithic porous capillary columns loaded with chromatographic particles based on sol-gel chemistry (Dulay et al., *Anal. Chem.*, 70, pp. 5103–5107, 1998).

Nevertheless, where separation columns are desired with packing material requiring frits, it would be desirable to have simple and reproducible procedures for fabricating frits.

The conventional method of frit fabrication for a particle-packed column involves thermal sintering of a section of the packing material, such as ODS (octadecyl silica particles). This approach has several disadvantages, including (1) difficulty in generating the frit reliably and reproducibly, (2) alteration of the characteristics of the stationary phase within the frit itself, (3) difficulty in controlling the porosity of the frit, (4) weakness of the capillary at the location of the frit, (5) band broadening caused by the frit, (6) bubble formation and adsorption of polar analytes on the frit. These problems can directly affect the column performance and column-to-column reproducibility.

BRIEF SUMMARY OF THE INVENTION

In one aspect of the present invention, a separation column is provided that comprises a separation channel having a channel wall and a separation medium in the channel, and wherein the separation column includes a photopolymer component. In one embodiment, the photopolymer component is a frit adapted to retain the separation medium. The frit has a controlled porosity and is preferably derived either from a methacrylate monomer that is polymerized via photoinitiation or from a methacrylate-substituted silicate that is photocurable. Because polymerization is initiated or cured by means of radiation, the position of the polymeric component can be localized and the porosity reproducibly controlled. Further, polymerization can be accomplished without removing the typical protective polyimide coating.

Another aspect of the invention is a method of fabricating frits in fused-silica capillaries, and more particularly in fabricating controlled porosity frits. Advantages of the invention include (i) easy and rapid preparation, (i) short reaction times, (iii) UV transparency of the photopolymer, and (iv) fine control of pore sizes. This results in a short total frit preparation time, and avoids the use of elevated temperatures.

BRIEF DESCRIPTION OF THE SEVERAL VIEWS OF THE DRAWINGS

FIG. 2 is a graphical representation showing in panel (A) a plot of absorbance versus retention time for one column and panel (B) for another column where the two analytes were thiourea and 2-methyl-naphthalene (in order of elution);

FIG. 3 are three representative electrochromatograms using an embodiment of the invention (column 2 of FIG. 2, panel (B)), where the analytes were thiourea, benzyl alcohol, benzaldehyde, and 2-methyl-naphthalene (in the order of elution); and FIG. 4 (panels A and B) are two representative electrochromatograms where in panel A Taxol (a promising anticancer drug) was run, whereas panel B was a Taxol analog (Baccatin D), both in relatively large-bore capillaries having frits of the present invention.

DETAILED DESCRIPTION OF THE INVENTION

Figure 1:
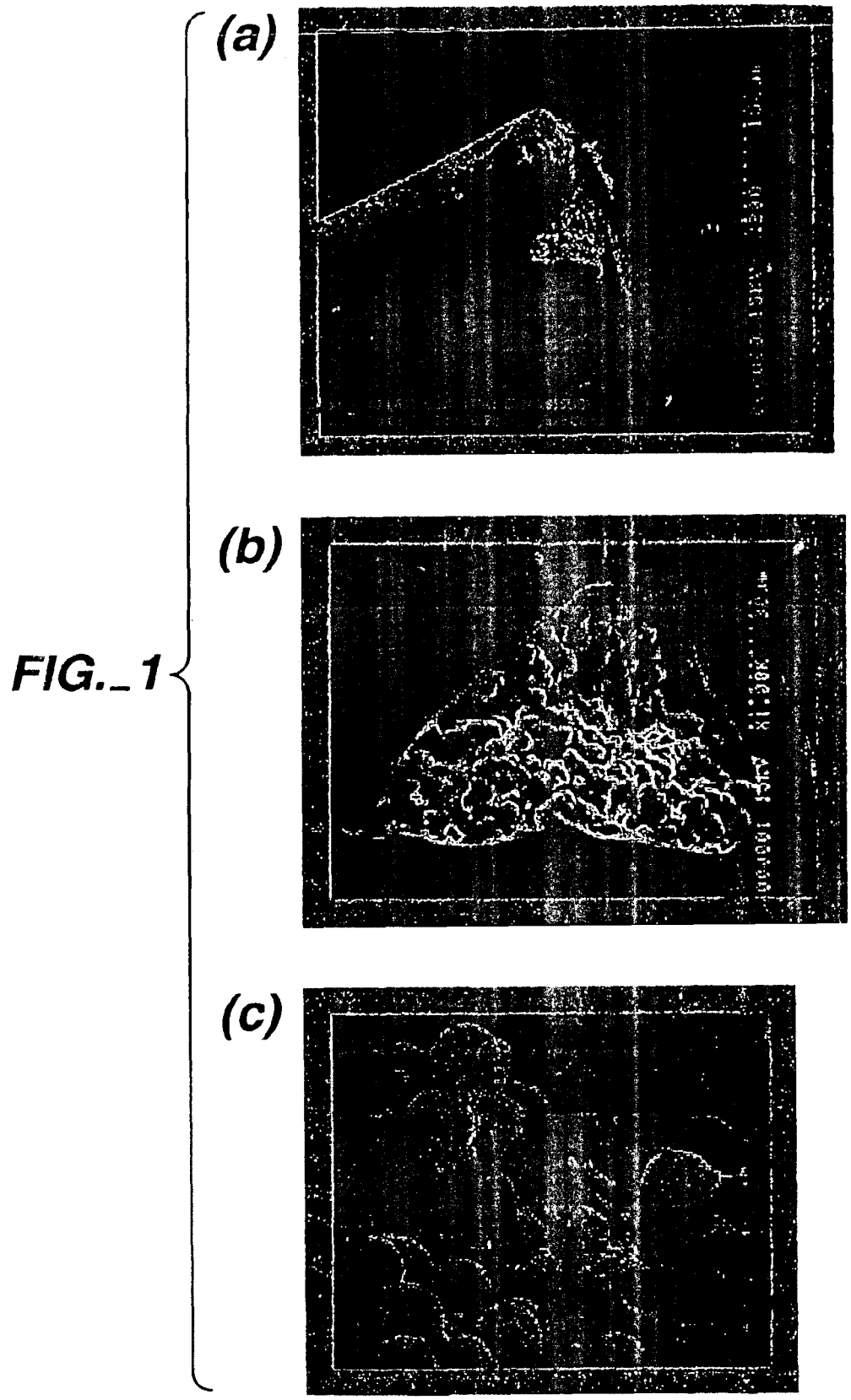
FIG. 1, panels (A), (B), and (C) are SEM micrographs where panel (A) is an oblique view of a photopolymer outlet frit in a capillary (with no particles present), panel (B) is a 5× magnified view of (A), and panel (C) is a cross-section of a photopolymer inlet frit with embedded chromatographic particles.

Capillary zone electrophoresis (CZE) has long been proven to be an attractive analytical technique for separating ionic species by their electrophoretic mobilities. The limitation of CZE, however, has been its ineffectiveness in separating neutral compounds. To this end, capillary electrochromatography (CEC), which combines both CZE and chromatography, has been developed to improve the separation of neutral species. A combination of mechanisms based partitioning and electrophoretic mobility can be used to describe the separation that occurs in CEC.

An existing technique for the preparation of retaining frits in packed capillary columns involves the sintering of silica beads within the columns. This sintering method is the common technique presently employed for the preparation of capillary column frits. Disadvantages of the sintered silica frits include the irreproducibility of the frit porosity and length and the need for very high temperatures.

We have used polymer photochemistry to prepare photopolymer frits in capillary columns. The photopolymer method has several advantages over the existing sintered silica methods, including (i) easy and rapid preparation, (ii) short reaction times at room temperature, (iii) UV transparency of the photopolymer, (iv) fine control of pore sizes, and (v) control of frit lengths and frit position.

In one embodiment of the present invention, photopolymer frits are prepared from a mixture of methacrylate monomers, porogenic solvents, and a photo initiator. Methacrylate monomers are known for use in the preparation of chromatographic separation media (Viklund et al., *Chemistry of Materials*, 9, pp. 463–471, 1997). Viklund et al. studied a variety of polymers prepared by photopolymerization and found them suitable as sorbants in analytical chemistry, and Viklund et al. is incorporated herein by reference in its entirety.

One aspect of our research concentrated on the preparation of the suitable frits and their effects on CEC separations. We chose a mixture of isooctane and toluene as a particularly preferred porogenic solvent for the preparation of porous polymers based on methacrylate. The pore sizes in the polymer mixture may be controlled through the use of porogenic solvents and by variations in the molar ratios of the monomers and the porogens. For example, by varying the proportions of these solvents, frit pore sizes of between about 1.0 and 5.0 microns, more preferably 2.5 and 4.0 $\mu$m, have been used in our experiments. The relationship of the component ratios and pore sizes has been discussed, for example, by Viklund et al., p. 464. Photopolymerization can be achieved even in silica capillaries without removal of the polyimide coating. This procedure is particularly advantageous for the preparation of inlet frits. It was found that, by the hydrolysis of glycidyl methacrylate, the hydrophilicity of the frit could be increased. This minimized the retaining effect of frits on the columns with reversed-phase chromatographic materials.

In another embodiment of the present invention, photopolymer frits are prepared from photocuring a methacrylate-substituted silicate, via a sol-gel reaction. Suitable photocured sol-gels are known and useful for practicing this aspect of the invention, such as described by Etienne et al., *J. Sol-Gel Sci. & Tech.*, 13, pp. 523–527 (1998), which is incorporated in its entirety by reference. Briefly, a monomer such as 3-(trimethoxysilyl) propyl methacrylate (MAPTMS) is irradiated to form a sol-gel matrix. Such a reagent is similar to the methacrylate-based reagent already described in the first embodiment of the present invention, and is photocurable. Broadly, the metal alkoxide sol-gel process is described by Brinker et al., *Sol-Gel Science*, Academic Press, Inc., New York (1990). When the gel is cured, a hard porous glass is obtained.

It is a common practice to remove the polyimide coating by chemical or thermal means in the detection area of the capillary because the polyimide allows for only a small transmittance of UV light into the capillary. In the preparation of frits in packed capillary columns used in CEC, the high heat required to center silica beads in the capillary columns leads to the removal of the polyimide coating, which imposes the fragile fused-silica at the portion of the capillary that contains the silica frit. However, in practicing the invention through use of photopolymers as components (such as for an inlet and outlet frit or as the supporting matrix itself), there is no need to remove the polyimide coating since the photochemical used to prepare the polymers can be conducted at relatively low levels of UV light. Thus, the capillary outer surface coatings remain intact and the mechanical strength of the column is maintained.

Images of a photopolymer frit embodiment based on the polymerization of methacrylate monomers with and without ODS particles are illustrated by the electron micrographs shown in FIG. 1, panels (A)–(C). FIG. 1, panel (A) shows the photopolymer in a 75 $\mu$m i.d. capillary, and FIG. 1, panel (B) provides a magnified view of the polymer. FIG. 1, panel (C) shows the polymer structure in the presence of 1.5 $\mu$m ODS particles. This micrograph also demonstrates that the photopolymer loses its spherical shape in the presence of the ODS particles and the pores entrap the silica beads and hold them within their domains.

After the polymerization had been completed, buffer solution was flushed (using a hand-held manual syringe pump) through a capillary column with one frit and no ODS particles present. There was almost no increase in the back-pressure observed as compared with the empty capillary without a photopolymer frit. This observation indicates that the frit does not significantly increase the flow resistance of the system. Although no specific functionalization of the inner capillary surface preceding the polymerization was carried out, the outlet frit easily withstands a short exposure of a high pressure (>6000 psi) used during the column packing. This behavior demonstrates that the monolithic porous polymer frit is strongly bound to the inner surface of the bare capillary wall. No particles of the packing were found to pass through the frit pores during either the packing procedure or the CEC applications, despite their size, which is smaller than that of the mean pore size. This results from the cooperative action of several effects such as the tortuous paths of the pores and the presence of bottleneck-shaped pores within the monolithic structure. Five columns were prepared with this packing procedure and, in all cases, the photopolymer frits exhibited similar mechanical stabilities under our experimental conditions.

In contrast to some other procedures, the UV photoinitiated polymerization does not require elevated temperature for the reaction to be completed. Therefore, the mobile phase used for packing remains in both the inlet frit and the packing during polymerization. Consequently, the conditioning time for the column prior to its use is shortened significantly.

No bubble formation occurred during all the separation runs using 1.5 μm ODS packed capillary columns with photopolymer frits based on methacrylate polymerization. The suppression of bubble formation might be due to both the addition of SDS in the running buffer and the replacement of sintered-silica frits with photopolymer frits.

The efficiency, N, the plate height, H, and the reduced plate height, h, of a packed column (column 2) embodiment with photopolymer frits based on the polymerization of methacrylate monomers are listed in Table 1.

TABLE 1

Column Efficiency, Plate Height, and Reduced Plate Height of Column 2*

| Analyte | N/m | H (μm) | h (dimensionless) |
|---|---|---|---|
| thiourea | 220 000 | 4.5 | 3.0 |
| 2-methylnaphthalene | 205 000 | 4.9 | 3.3 |

*Column 2: 75-μm i.d. × 27-cm (20 cm packed with 1.5-μm ODS particles). Mobile phase: 20% (v/v) 5 mM phosphate with 2 mM SDS (pH 7.0) and 80% (v/v) acetonitrile.

FIG. 2 compares the separation of two neutral compounds, thiourea and 2-methylnaphthalene, achieved in columns furnished with porous polymer frits characterized by mean pore diameters of 2.5 (FIG. 2, panel (A)) and 4.0 μm (FIG. 2, panel (B)), respectively. The column with 4-μm frits exhibits shorter retention times and a better column efficiency compared with those of the other column.

A systematic study of the run-to-run reproducibility for the analysis of a mixture of neutral molecules consisting of thiourea, benzyl alcohol, benzaldehyde, and 2-methylnapththalene was carried out over a period of 3 days. FIG. 3 shows electrochromatograms of runs 10, 30, and 50 of the Table 1 embodiment. There is almost no variation in retention times of all test compounds. Table 2 shows the relative standard deviations of the capacity factor, $k^1$, the efficiency, N, and the resolution, R, for each compound. These RSDs for all three monitored variables, averaged over 60 runs, were 3.5%, 3.3%, and 5.5%, respectively.

TABLE 2

Relative Standard Deviation of Capacity Factor ($k^1$), Column Efficiency (N), and Resolution ($R_1$) over 80 Separations for Column 2*

| Relative Standard Deviation (%) Analyte | $k^1$ | N | $R_s$ |
|---|---|---|---|
| thiourea |  | 2.0 | 3.0 |
| benzyl alcohol | 3.2 | 5.5 | 3.2 |
| benzaldehyde | 2.1 | 5.3 | 2.7 |
| 2-methylnaphthalene | 2.6 | 3.6 | 2.8 |

*Column 2: 75-μm i.d. × 27-cm (20 cm packed with 1.5-μm ODS particles). Mobile phase: 20% (v/v) 5 mM phosphate with 2 mM SDS (pH 7.0) and 80% (v/v) acetonitrile.

The integrity of the packed column remained unchanged, and the column is believed to be useful for a much longer period of time. In FIG. 3, the efficiencies of thiourea, benzyl alcohol, benzaldehyde, and 2-methylnaphthalene are 200 000 plates/m, 160 000 plates/m, 60 000 plates/m, and 20 000 plates/m, respectively. The unretained compound, thiourea, gave the highest efficiency. The efficiencies dropped for the compounds that were more retained than thiourea. The significant efficiencies drop of the last two peaks compared with those of FIG. 2 are mainly due to the use of a lower percentage (50%) of acetonitrile in the running buffer. Furthermore, the peak for 2-methylnaphthalene shows tailing that is mainly due to its adsorption to the surface of the ODS particles.

Experimental

Materials. The monomers trimethylolpropane trimethacrylate (TRIM) and 2,3-epoxypropyl methacrylate (glycidyl methacrylate, GMA) were of the highest purity available from Aldrich (Milwaukee, Wis.). Toluene and 2,2,4-trimethylpentane (isooctane) from Sigma (St. Louis, Mo.) were used as porogenic solvents. The fused capillaries used in this study were purchased from Polymicro Technologies (Phoenix, Ariz.). The 1.5 μm spherical ODS particles were provided by Micra Scientific, Inc. (Lafayette, Ind.), α-Methoxy-α-phenylactophenone (benzoin methyl ether, 99%), thiourea, benzaldehyde, benzyl alcohol, 2-methylnaphthalene, sodium phosphate, and acetonitrile (HPLC grade) were purchased from Aldrich (Milwaukee, Wis.). Water was purified with an Ultrapure water system from millipore (Milford, Mass.).

Polymerization Procedure. The photopolymerization procedure was carried out as previously described (Viklund et al., Chem. Mater., 9, pp. 463–471, 1997). In situ free-radical polymerization was initiated by irradiating the monomer solution in 4 mm i.d. quartz tubes and 75 μm i.d. capillaries for 60 minutes at room temperature in a Spectrolinker XL 1500A (Spectronics Corp., Westbury, N.Y.) with six 15 W fluorescent blacklight tubes, producing UV light of predominantly 365 μm(?) wavelength. After one hour, the porogen, unreacted monomers, and other soluble compounds were removed from the pores by washing with ethanol using an HPLC pump.

Pore-Size Measurement. The pore-size distribution of the porous polymer was determined for the samples prepared in the 4 mm tubes from the same polymerization mixtures as the capillaries, by mercury intrusion porosimetry using an automated custom-made combined BET sorptometer-porosimeter (Porous Materials, Inc., Ithaca, N.Y.).

Frit Fabrication and Column Packing. An outlet frit was prepared by introducing the monomer mixture into the capillary. The two ends of the capillary were sealed with Parafilm. The capillary was then covered by aluminum foil, leaving 1 mm of the outlet section without polyimide coating exposed to the UV light. The rest of the outlet section that was masked during photopolymerization because the detection window for CE experiments. After an hour of polymerization at room temperature, the unreacted monomer solution was flushed from the column by a syringe pump. After slurry packing the column, 1.5 μm ODS particles were filled up to the inlet end of the capillary. The same procedure to create the outlet frit was employed to form the inlet frit. The resulting columns were preconditioned with the mobile phase by pressurizing the column inlet to approximately 500 psi with a manual syringe pump (Unimicro Technologies, Inc., Pleasanton, Calif.) for a few hours prior to their use. It was noticed that the polymerization also took place without removing the polyimide coating, but the process took about four to six hours.

Capillary Electrochromatography. The CEC experiments were performed with a Beckman model 2000 P/ACE capillary electrophoresis system Beckman Coulter, Fullerton, Calif.) equipped with an UV absorbance detector. The 75 μm i.d. packed capillary column was installed in the cartridge holder that was then inserted into the instrument. There is no pressure applied to the packed column in this system. Once the packed column was installed, it was further conditioned by driving the mobile phase through the capillary at an applied voltage of 5 kV for 1 hour prior to use. Samples were introduced electrokinetically at the anodic end of the capillary column. The mobile phase employed in these separations was a 5 mM phosphate and 2 mM SDS buffer (pH 7.0) containing 80% (v/v) acetonitrile. Separations were performed at an applied voltage of 10 kV and at a temperature of 20° C. The analytes were detected by monitoring their absorbance at 254 nm.

A mixture of neutral compounds was separated on two columns, 1 and 2. Column 1 was a 75 $\mu$m i.d.×27 cm (20-cm packed with 1.5 $\mu$m ODS particles fused-silica capillary. The frit pore size of this column was 2.5 $\mu$m. Column 2 was the same as column 1, except the frit pore size was 4.0 $\mu$m.

Semi-preparative CEC work was carried out using home-made CE instrument. The capillary column (550 $\mu$m i.d. and 650 $\mu$m o.d.) was packed with 1.5 $\mu$m diameter ODS particles using slurry packing method. The frits of these large-bore capillary columns were prepared from a mixture of methacrylate monomers, porogenic solvents, and a photo initiator (Vildund et al.) in the same manner as already described. The running buffer was a mixture of 20% 5 mM phosphate and 80% acetonitrile. The total length of the capillary was 34 cm. The applied voltage across the CEC column was 2 kV. The sample injection volume was 150 nl. Electrochromatograms of Taxol and Baccatin III analysis, respectively, are shown by panels A and B of FIG. 4.

It is to be understood that while the invention has been described above in conjunction with preferred specific embodiments, the description and examples are intended to illustrate and not limit the scope of the invention, which is defined by the scope of the appended claims.

What is claimed is:

1. A separation column comprising:
   a separation channel extending between an inlet and an outlet and having a channel wall; and,
   a separation medium in the channel, said channel having at least one photopolymer frit adapted to retain the separation medium in the channel, the at least one frit having a controlled porosity.

2. The separation column as in claim 1 wherein the photopolymer frit is bound to an inner surface of the channel wall.

3. The column as in claim 1 wherein the photopolymer frit is adjacent to the inlet, the outlet, or both.

4. The column as in claim 1 wherein the controlled porosity of the photopolymer frit is a mean pore size of between about 1.0 $\mu$m and 5.0 $\mu$m.

5. The column as in claim 1 wherein the separation channel is a fused-silica capillary having an internal dimension in the range of between about 5 and 300 $\mu$m, and the photopolymer frit is of a structure sufficient to withstand high pressure during packing of the separation medium in the channel.

6. The separation column as in claim 5 wherein the photopolymer frit is derived from a methacrylate monomer or a methacrylate-substituted silicate.

7. The separation column as in claim 6 wherein the photopolymer frit is derived from a methacrylate monomer polymerized via photoinitiation.

8. The column as in claim 6 wherein the photopolymer frit is derived from a photocurable methacrylate-substituted silicate.

9. The column of claim 1, said column having a first portion that is filled with said separation medium and a second portion adjacent to said first portion that transmits radiation.

10. The column of claim 9 wherein said second portion does not contain said separation medium.

* * * * *